United States Patent [19]
Paul et al.

[11] Patent Number: 5,735,883
[45] Date of Patent: Apr. 7, 1998

[54] IMPLANTABLE CARDIAC STIMULATOR WITH IMPEDANCE BASED AUTOTHRESHOLD

[75] Inventors: Patrick J. Paul; David Prutchi, both of Lake Jackson, Tex.

[73] Assignee: Sulzer Intermedics Inc., Angleton, Tex.

[21] Appl. No.: 766,870

[22] Filed: Dec. 13, 1996

[51] Int. Cl.$^6$ .................................................. A61N 1/37
[52] U.S. Cl. ........................................................ 607/28
[58] Field of Search ................................. 607/5, 28, 17

[56] References Cited

U.S. PATENT DOCUMENTS

| | | |
|---|---|---|
| 4,140,132 | 2/1979 | Dahl . |
| 4,373,531 | 2/1983 | Wittkampf et al. . |
| 4,537,201 | 8/1985 | Delle-Vedove et al. . |
| 4,686,987 | 8/1987 | Salo et al. . |
| 4,688,573 | 8/1987 | Alt . |
| 4,858,610 | 8/1989 | Callaghan et al. . |
| 4,901,725 | 2/1990 | Nappholz . |
| 4,979,507 | 12/1990 | Heinz et al. . |
| 5,154,171 | 10/1992 | Chirife . |
| 5,197,467 | 3/1993 | Steinhaus et al. . |
| 5,201,808 | 4/1993 | Steinhaus et al. . |
| 5,413,592 | 5/1995 | Schroeppel ............... 607/18 |
| 5,476,487 | 12/1995 | Sholder ..................... 607/28 |
| 5,507,785 | 4/1996 | Deno ......................... 607/24 |
| 5,531,772 | 7/1996 | Prutchi ..................... 607/17 |

OTHER PUBLICATIONS

E. Alt, et al. "Feasibility of Using Intracardiac Impedance Measurements for Capture Detection", Pace vol. 15, Part II, Nov. 1992, pp. 1873–1879.

Primary Examiner—Scott M. Getzow
Attorney, Agent, or Firm—John R. Merkling

[57] ABSTRACT

An implantable pacemaker with apparatus for detecting capture or adjusting the strength or duration of pacing pulses by assessing the mechanical evoked response that may be distinctly sensed through impedance sensing, pressure sensing, plethysmography or other suitable methods. When capture is to be detected or the strength or duration of the pacing pulses is to be adjusted, two pacing pulses are delivered to the heart in each cycle of a series of cardiac cycles. The first pulse is varied in strength or duration or both. The second pulse is maintained at a consistently high strength or duration to assure capture. The impedance of the heart is measured during a time window following the first pulse which is predicted to include a recognizable feature of the impedance waveform of the heart following a stimulating pulse. The magnitude of the first pulse is gradually changed until capture is lost. When the stimulation effect of the first pulse on the heart changes, the impedance measured during the window will change distinctly, indicating that a stimulus threshold has been detected.

22 Claims, 4 Drawing Sheets

IMPLANTABLE CARDIAC STIMULATOR WITH IMPEDANCE BASED AUTOTHRESHOLD

FIELD OF OUR INVENTION

Our invention relates to rate responsive cardiac pacemakers, and more particularly to cardiac pacemakers which automatically adjust the amplitude of pacing stimulus pulses to conserve energy, and particularly in response to measured impedance changes in the heart.

BACKGROUND OF OUR INVENTION

Implanted cardiac pacemakers are employed to assist patients suffering from severe bradycardia or chronotropic incompetence. A cardiac pacemaker "captures" the heart by delivering an electrical pulse to the myocardium of either the atrium or the ventricle during an interval in the cardiac cycle when the cardiac tissue is excitable. The electrical pulse causes depolarization of cardiac cells and contraction of the chamber if the energy of the pacing pulse exceeds a threshold value. It is important that the pulse reliably stimulate contraction or "capture" the heart. At the same time, it is desirable to use as little energy as possible, to extend the useful life of the pacemaker.

The threshold for capture, however, varies in a patient over time. It is therefore desirable to periodically adjust the pulse magnitude and duration to optimize use of pulse energy. Adjustment can be effected manually through the use of an external programmer. An operator verifies capture by visually assessing a detected ECG waveform. It is desirable, however, to provide a pacemaker with means that allow it to automatically determine threshold levels, either in response to a command from the external programmer or as part of the pacemaker's internal procedures and treatment.

For such a procedure to be safe and effective, however, it is important for the pacemaker to be able to verify that capture has taken place, that is, that the heart has been stimulated by a particular pulse. Capture verification has been generally accomplished by detecting and evaluating the electrical evoked response of the heart resulting from stimulation. If capture has not occurred, there will be no evoked potential to detect. Theoretically, each time a stimulating pulse is delivered to the heart, the heart could be monitored to detect the presence or absence of the evoked response. In practice, however, reliable detection of the evoked response is not a simple matter, especially if the evoked response is to be detected with the same electrode used for stimulating the heart. The evoked potential is small in amplitude relative to the residual polarization charge on the electrode resulting from the depolarization pulse.

Several patents have dealt with techniques to differentiate the evoked potential from other potentials and artifacts. For example, U.S. Pat. No. 4,858,610 describes a method to reduce the polarization of the electrode after the delivery of stimulation. Similar techniques are described in U.S. Pat. No. 4,373,531. Other patents teach methods for enhancing the signal components of the evoked potential to make it easier to distinguish from other polarization potentials and artifacts. For example, U.S. Pat. No. 4,537,201 teaches the linearization of the exponentially decaying sensed signal by applying the sensed signal through an anti-logarithmic amplifier in order to detect the non-linear component caused by the evoked potential. Similarity between the characteristics of the evoked response and the characteristics of interfering signals, however, make it difficult to detect capture with a high degree of precision and confidence.

An alternative method has been proposed by Sholder in U.S. Pat. No. 5,476,487. Instead of isolating the evoked R-wave, Sholder proposed detecting the time periods between a pair of pacing pulses and the evoked T-wave. This method requires a specialized sense amplifier for T-wave detection. Not only is the T-wave difficult to detect, but also T-waves vary widely from patient to patient.

All of the previously described methods are more difficult to apply to the atrium than to the ventricle, both because the electrical signals generated in the atrium are weaker and because atrial signals may be masked by concurrent electrical activity in the ventricle. There remains a need, therefore, for a reliable means for detecting capture in the heart, in either the atrium or the ventricle or both.

To do this, our invention detects an impedance characteristic of the heart associated with capture rather than an evoked electrical signal. Impedance sensing has been used principally to control the rate of cardiac pacing, but it has also been used to detect capture by the pacing pulse.

"Rate adaptive" or "rate responsive" pacemakers were developed. These pacemakers sense some parameter correlated to physiologic need and adjust the pacing rate of the pacemaker. Numerous parameters have been selected to attempt to correlate pacing rate to the actual physiologic need of the patient. Blood pH, blood temperature, QT interval, vibration, respiration rate, or accelerations due to physical activity have been employed with varying degrees of success. Among these parameters are the stroke volume of the heart and the minute volume of respiration, both parameters being inferred from impedance measurements. The stroke volume of the heart is defined as the volume of blood expelled by the ventricle in a single beat.

For example, in Salo et al., U.S. Pat. No. 4,686,987 a stroke volume responsive, rate adjusting pacemaker is described. An AC signal is inserted through an implanted lead. The changing volume of the heart alters the impedance between the lead electrode and another electrode or the can of the pacemaker, and the changing impedance modulates the detected AC signal. By isolating the resulting amplitude envelope, an indication of the changing impedance can be obtained. This fluctuation is deemed to be a function, at least in part, of the action of the heart.

Chirife, U.S. Pat. No. 5,154,171, proposed that metabolic demands should be related to the ejection fraction, as a more accurate measure of true physiologic need. The ejection fraction is the stroke volume divided by the end diastolic volume. The stroke volume is taken to be the end diastolic volume minus the end systolic volume. The observed impedance of the heart is deemed to be a function of volume of the heart and therefore to be an indication of the desired measurements when taken at an appropriate time.

The impedance of the body, however, is not solely related to the beating of the heart. Other motions and factors also change the impedance characteristics. One example is change due to respiration. It has been proposed that the minute volume of respiration could be detected by an appropriate impedance measurement. See, for example, U.S. Pat. No. 4,901,725 entitled "Minute Volume Rate Responsive Pacemaker" to Nappholz et al.

U.S. Pat. No. 5,201,808 to Steinhaus et al., describes several attempts to detect the minute volume due to respiration in an accurate manner. Steinhaus et al. also proposes a relatively high frequency wave form as the appropriate means for measuring the spatial impedance as a function of the patient's pleural pressure. Steinhaus et al. notes that different frequencies for the testing pulse are adapted to detecting different phenomenon. That is, one range of frequency may be more appropriate for detecting changes due to heart beats, another would be more appropriate for detecting minute volume.

U.S. Pat. No. 5,197,467 to Steinhaus, et al. describes charging a capacitor and discharging the capacitor through the heart or a portion of the body for a selected brief interval. The voltage remaining on the capacitor after the period of discharge can be detected through a buffer, converted to digital information, and used to estimate the impedance of that portion of the patient's body between the cathode and anode electrodes.

In U.S. Pat. No. 5,507,785, Deno disclosed a rate responsive pacemaker, sensitive to impedance changes in the heart as an indicator of cardiac stroke volume or minute volume, wherein common interfering signals such as the intra cardiac electrogram, myoelectric signals, pacing artifacts and other pacing after potentials are reduced or eliminated from the measurement of the impedance by the use of a biphasic test signal and measurement process. The cardiac pacemaker has a signal injector which produces biphasic test pulses of very brief duration, for example, between two and fifty microseconds. The pulses are preferably of similar duration and magnitude, though of opposite polarity. They are delivered by the signal injector across a selected set of electrodes. The pulses are preferably of substantially constant current. A detector senses voltage resulting from the applied biphasic current pulses in each phase.

In U.S. Pat. No. 5,531,772, one of us (Prutchi) disclosed a cardiac pacemaker which senses varying impedance of the heart by discharging an active capacitor through an electrode implanted within the heart to a second electrode or to the case or can of the pacemaker. The active capacitor is discharged for a selected short period of time after which the voltage remaining on the capacitor is buffered for further processing. Prior to discharge of this active capacitor, however, the cardiac pacemaker samples the electrical condition of the heart or the body of the patient between the two electrodes by charging a passive capacitor. The voltage on this passive capacitor is also buffered and held in a sample and hold circuit until the active capacitor has been discharged. The voltage on the passive capacitor is subtracted from the residual voltage on the active capacitor and the resulting voltage is held in a sample and hold circuit. The voltage held in the sample and hold circuit is communicated to a microprocessor for adjustment of the rate of the pacemaker. To minimize error in the measurement of voltage discharged from the active capacitor, the selected short period of time for discharge can be varied dynamically by the cardiac pacemaker.

Any of the forgoing methods of detecting impedance changes in the heart, heretofore used to control pacing rate, could be used in connection with our invention to adjust the strength and duration of the pacing pulse. In addition, any system which detects a change in the mechanical evoked response, rather than a change in the electrical impedance evoked response, could also be used.

SUMMARY OF OUR INVENTION

Our invention solves the problems of the previous devices for detecting capture or adjusting the strength or duration of pacing pulses by assessing the mechanical evoked response that may be distinctly sensed through impedance sensing, pressure sensing, plethysmography or other suitable methods. When capture is to be detected or the strength or duration of the pacing pulses is to be adjusted, two pacing pulses are delivered to the heart in each cycle of a series of cardiac cycles. The first pulse is varied in strength or duration or both. The second pulse is maintained at a consistently high strength or duration to assure capture. The impedance of the heart is measured during a time window following the first pulse which is predicted to include a certain recognizable impedance waveform feature of the heart following a stimulating pulse. The magnitude of the first pulse is gradually decreased until capture is lost. When the first pulse fails to captures the heart, the impedance measured during the window will change distinctly since the contraction of the heart would be caused not by the first pulse, but rather by the second, safety pulse. Consequently, the apparatus will always be comparing conditions caused by contraction, rather than comparing contraction and non-contraction. Therefore, similar conditions should be produced in each cycle, displaced temporally by the delay between the first and second pulses.

This procedure could also be implemented by beginning with a non-capturing first pulse and gradually incrementing the pulse until capture occurs. In either case, the heart is stimulated in each cycle, including those cycles in which the first pulse fails to achieve capture of the heart. If desired, the impedance of the heart could also be measured during a window between the first and second pulses. This impedance measurement could be used to eliminate variation in the detected impedance not attributable to the mechanical response of the heart.

It is an object of our invention to provide a cardiac stimulator which can detect the stimulus threshold of the heart.

A further object of our invention is to detect the stimulus threshold without loss of capture during a cardiac cycle.

Another object of our invention is to provide an apparatus that utilizes detected mechanical condition of the heart and utilizes that detected condition to detect the stimulus threshold of the heart.

Another important object of our invention is to detect the stimulus threshold of the heart using the detected impedance of the heart.

These and other objects and features of our invention will be apparent to the skilled artisan from the following detailed description taken with reference to the accompanying drawings.

DETAILED DESCRIPTION OF OUR PREFERRED EMBODIMENT

We will now describe the preferred embodiment of our invention with reference to the accompanying figures. Like numerals will be used to designate like parts throughout.

Figure 1:
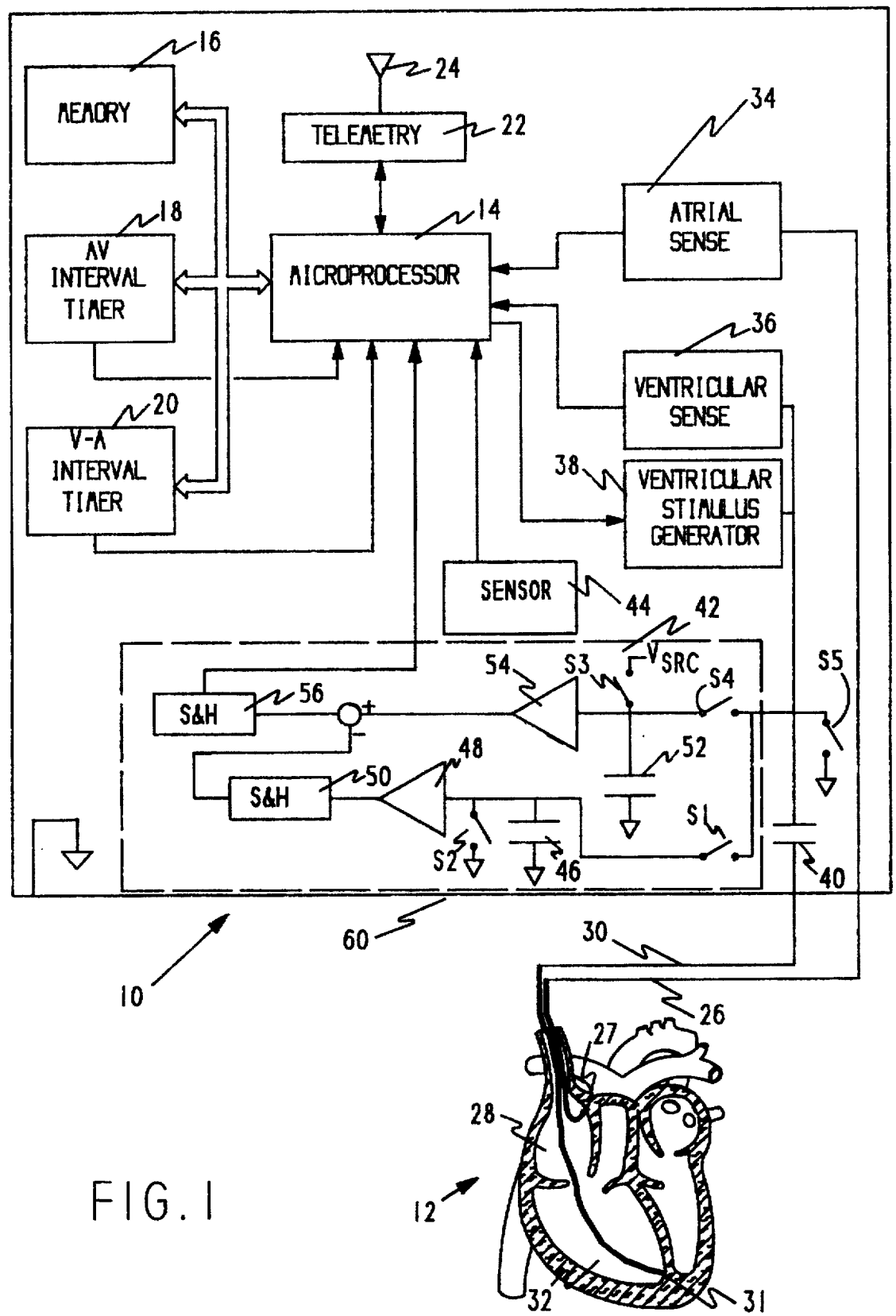
FIG. 1 is a block diagram of a first preferred embodiment of a pacemaker according to our invention.

Referring now to FIG. 1, a pacemaker, generally designated 10, is illustrated in schematic fashion with connection to a human heart 12. For ease of illustration, we have elected to describe our invention in connection with a pacemaker having atrial sensing and ventricular sensing and pacing. It should be understood, however, that our invention can be employed for sensing in the atrium, the ventricle or both and that both atrial or ventricular pacing could be provided without departing from the teachings of our invention. In addition, the features of our invention could also be combined with an implantable defibrillator/cardiovertor.

With this understanding, the illustrated pacemaker 10 comprises a microprocessor 14 which executes various control programs to regulate the action of the pacemaker. The microprocessor 14 is connected to additional memory 16 for the storage of programs and data as may be needed. As is known in the art, one or more internal clocks may be provided to permit timing of various events. For example, an A-V interval timer 18 may be provided. Similarly, a V-A interval timer 20 may also be provided, as known in the art. The microprocessor is provided with a telemetry circuit 22 so that communication can be had across an antenna 24 to an external programmer (not shown). Telemetry permits an attending physician to obtain data and information from the pacemaker and to control the pacemaker to set various selectable parameters, as known in the art. A command might also be issued to the pacemaker to implement an autothreshold search sequence, as more fully explained below.

The pacemaker 10 is connected to the heart 12 through a first lead 26 to an electrode 27 in the atrium 28 and through a second lead 30 to an electrode 31 in the ventricle 32. An indifferent electrode is provided to complete the electrical circuit. In the illustrated embodiment, a can 60 or outer casing of the pacemaker serves as the indifferent electrode. Bipolar leads can also be used with our invention as well as the unipolar leads illustrated here. Atrial sensing, through an atrial sense circuit 34, and ventricular sensing, through a ventricular sense circuit 36, provide information to the microprocessor concerning the condition and responsiveness of the heart. In addition, pacing pulses are provided to the ventricle from a ventricular stimulus generator 38. It is clearly within the capabilities of those skilled in the art to provide atrial pacing, should that be desired, or to provide cardioversion/defibrillation capabilities in response to the detected condition of the heart. Stimulation of the heart is passed through a coupling capacitor 40 in a conventional fashion. A switch S5, connected to ground, is periodically closed to discharge the capacitor 40 and balance stimulation pulses, producing a net zero charge at the electrode.

The microprocessor acquires information on the condition of the heart through an impedance circuit 42. The impedance circuit 42 detects changes in impedance primarily due to the changing shape of the heart, which is related to the physical shape of the heart as it beats and pumps blood. This information can be used to detect capture of the heart by stimulating pulses as explained below. In addition to the measurement of impedance, a sensor 44 may also be provided to obtain an indication of physiologic need and adjust the pacing rate. Such a sensor may be an accelerometer, as described by Dahl, U.S. Pat. No. 4,140,132, (incorporated herein by reference) a temperature sensor, as described by Alt, U.S. Pat. No. 4,688,573 (also incorporated herein by reference), or any other suitable sensor of a parameter which may be correlated to physiologic need of the patient.

The impedance circuit 42 comprises a first capacitor 46 which we will call a passive capacitor. This capacitor 46 is connected on one side to the lead 30 through a switch S1 and coupling capacitor 40; and to ground through a second switch S2. The capacitor 46 is also connected to a buffer 48 in common with the two switches S1 and S2. On the other side of the capacitor 46, the capacitor 46 is connected to ground. The buffer 48 communicates with a sample and hold circuit 50. The function of the separate sample and hold circuit 50 can be performed by the passive capacitor 46 and the buffer 48, if the sampling time is short and the impedance of the buffer 48 is high. Each of the two switches S1 and S2 and the sample and hold circuit 50 are controlled by the microprocessor 14. Such connections are well known in the art and are not illustrated for the sake of clarity. A second capacitor 52, which we will call an active capacitor, is also connected to the lead 30 and coupling capacitor 40 through a switch S4. Preferably, the passive capacitor is of similar magnitude to the active capacitor, and most preferably the passive capacitor has the same capacitance as the active capacitor. This enables the passive capacitor to serve as an accurate model of the effect of background voltages on the active capacitor, as will be more fully explained below.

The side of the active capacitor 52 connected to the lead is further connected through a switch S3 to a voltage source, labeled $V_{SRC}$ in FIG. 1. Finally, the capacitor 52 is connected in common with the two switches S4 and S3 to a buffer 54. The other side of the capacitor 52 is connected to ground. The output of the buffer 54 is combined with the output of the sample and hold circuit 50, as will be more particularly described below, by subtracting the voltage of the sample and hold circuit 50 from the output of the buffer 54. The resulting voltage is held in a second sample and hold circuit 56 until required by the microprocessor. Typically, the analog value of the voltage held by the sample and hold circuit 56 is converted to a digital value for further processing. As explained above, the switches S3 and S4 and the sample and hold circuit 56 are controlled by the microprocessor 14 in a manner similar to that of switches S1 and S2 and sample and hold circuit 50.

Figure 2:
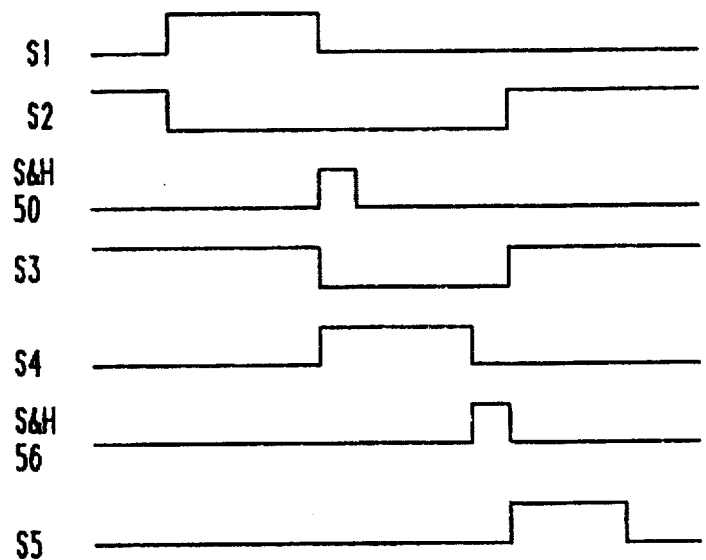
FIG. 2 is a timing diagram.

The operation of the impedance circuit 42 can be understood with respect to a timing diagram, FIG. 2. As explained in U.S. Pat. No. 5,531,772, the impedance circuit determines the impedance of the heart at a relatively high rate, on the order of 100 sample cycles per second when used in connection with pacemaker rate control. For autothreshold, two short periods or windows of about 10 msec, each at a selected time or delay after delivery of a stimulating pulse are used, as explained below. A single sample cycle is described with respect to FIG. 2. As each cycle begins, passive capacitor 46 is in a discharged state while active capacitor 52 is charged to a preselected voltage level, $V_{SRC}$, which may be about 0.5 V or less. Initially, during the cycle, S1 is closed for a preselected period, for example, 15 μsec. This is indicated in the timing diagram of FIG. 2 by the line S1 going high. Simultaneously, switch S2 is opened as indicated by the line S2 going low. This effectively connects the passive capacitor 46 through the lead 30 to the electrode 31 within the heart 12. The passive capacitor 46 assumes an electrical value proportional to that of the electrode 31 during the time that switch S1 is closed.

After switch S1 opens, the electrical condition of the passive capacitor 46 appears through the buffer 48 at the sample and hold circuit 50. The sample and hold circuit 50 is therefore triggered by the microprocessor to capture this voltage as indicated by the line S/H 50 going high. While the passive capacitor 46 is charged from the electrical condition of the heart, the active capacitor 52 is charged from $V_{SRC}$ through S3 as indicated by the high condition of line S3 in FIG. 2. When switch S1 opens, switch S3 also opens as indicated by the low condition of line S3. Simultaneously, switch S4 closes, as shown by line S4 in FIG. 2, for a preselected period of time, for example 15 μsec. If the active capacitor 52 has the same capacitance as the passive capacitor 46, as described above, and if the resistance of the two switches S4 and S1 are equal, then S1 is preferably activated for the same length of time as S4. The active capacitor 52 discharges through switch S4 and lead 30 through the electrode 31 in the heart. Electrical current passes from the electrode 31 within the heart to an anode on lead 30 or to the can 60 of the pacemaker which acts as an indifferent electrode.

When S4 opens, S3 does not immediately close. Rather, the electrical condition of the active capacitor 52 is passed through buffer 54. The electrical value retained in the sample and hold circuit 50, representing the electrical condition of the heart, is subtracted from the output of buffer 54 and the resulting value is captured by the sample and hold circuit 56, as represented by line S/H 56 going high. After the sampling by sample and hold circuit 56 is complete, initial conditions on the capacitors 46, 52 can be restored by connecting the passive capacitor 46 to ground through S2 (indicated by line S2 going high) and the active capacitor 52 to $V_{SRC}$ through switch S3 (indicated by line S3 going high). In addition, pacing and impedance sensor pulses are usually passed to the heart through an AC-coupling capacitor 40. Switch S5 is used to discharge this capacitor and to produce a balanced pulse which results in zero net charge flow through the tissue. This is indicated by line S5 going high, closing switch S5. Switch S5 opens when line S5 goes low.

S4 being closed (see FIG. 2) represents a selected short period of time during which the active capacitor 52 is discharged through the heart. The voltage on the active capacitor 52 decays exponentially according to the following formula:

$$V_{CA}(t) = V_0 e^{-t/RCa}$$

Where $V_{CA}$ is the voltage remaining on the active capacitor after a time t; $V_0$ is the initial voltage on the capacitor; R is the lumped resistance of the circuit, and Ca is the capacitance of the active capacitor 52. There is an error associated with making the measurement of $V_{CA}$ as there is in making any measurement. This error can be minimized, however, by making the measurement after an elapsed time T equal to one time constant that is, at t=T=RCa. The desired measured value is R determined as follows:

$$R = -t/(Ca \ln (V_{CA}(t)/V_0))$$

The fractional error in the measurement of R, that is, d(ln R), is a function which has a minimum at t=T=RCa. The function is:

$$d(\ln R) = -[\ln (V_{CA}(t)/V_0)]^{-1}[V_{CA}(t)/V_0]^{-1}$$

Figure 3:
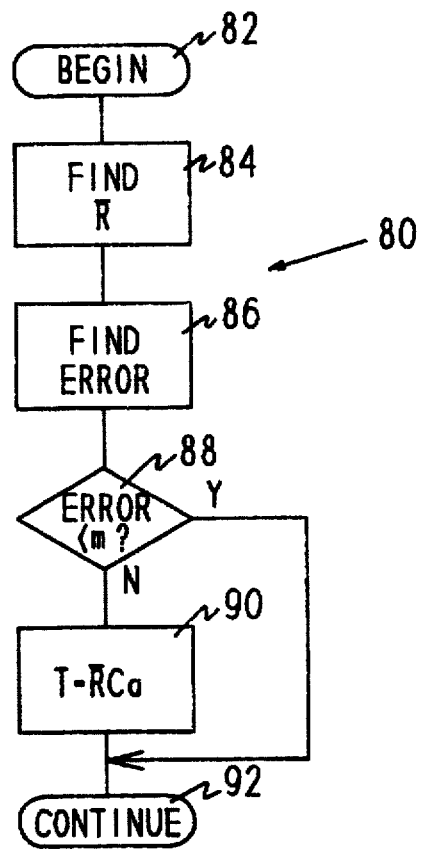
FIG. 3 is a flow chart of an algorithm for minimizing error in voltage measurement on an active capacitor.

The value Ca, the capacitance of the active capacitor, is constant, but the value R, the impedance of the circuit including the heart, is changing. The error associated with the measurement of $V_{CA}$ (and thus also the error associated with the impedance) can be minimized by programming the microcomputer 14 to dynamically adjust the time during which S4 is open. A suitable procedure, generally designated 80, is illustrated diagrammatically in FIG. 3.

The procedure 80 is part of the general operation of the microcomputer 14. When the procedure 80 begins 82, an average or representative value of the impedance R is determined 84. This could, for example, be the rolling average of the measured value of the impedance for a predetermined number of cycles. The fractional error d(ln R) is then computed 86. The fractional error is compared 88 to an acceptable value m. If the fractional error is less that the acceptable value m, the value t, that is the time switch S4 is open, is unchanged. If the fractional error is greater than the acceptable value m, a new value of t is calculated 90 such that t=RCa. The microprocessor proceeds 92 with other processing, using the new value t to determine the impedance from the measured value of $V_{CA}$ after a discharge time t.

Figure 4:
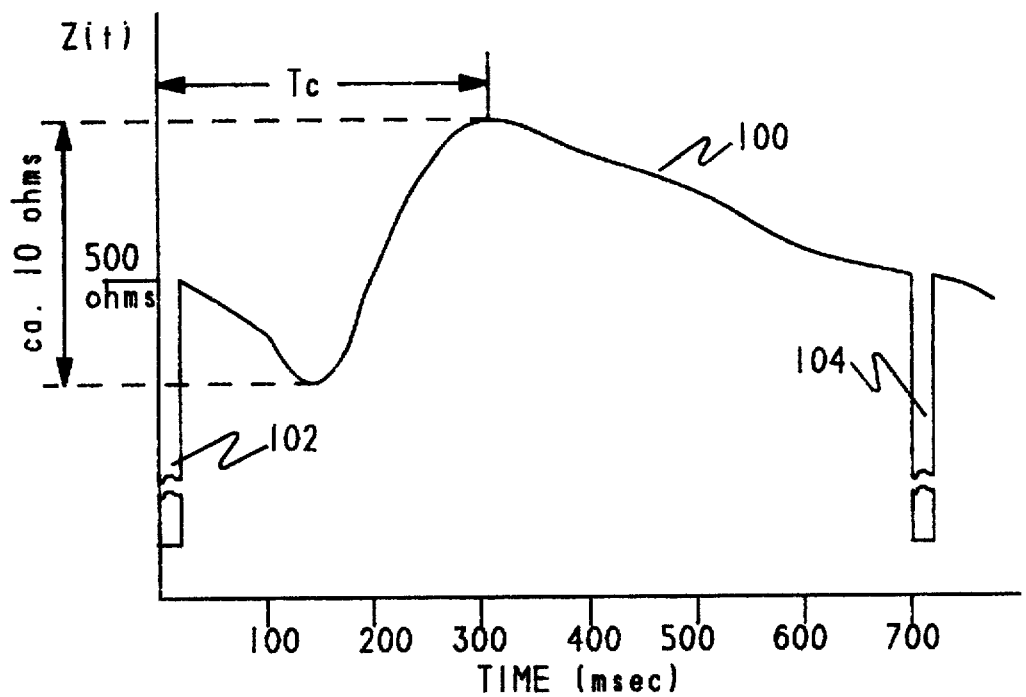
FIG. 4 is a graph of impedance after a stimulating pulse.
Figure 5:
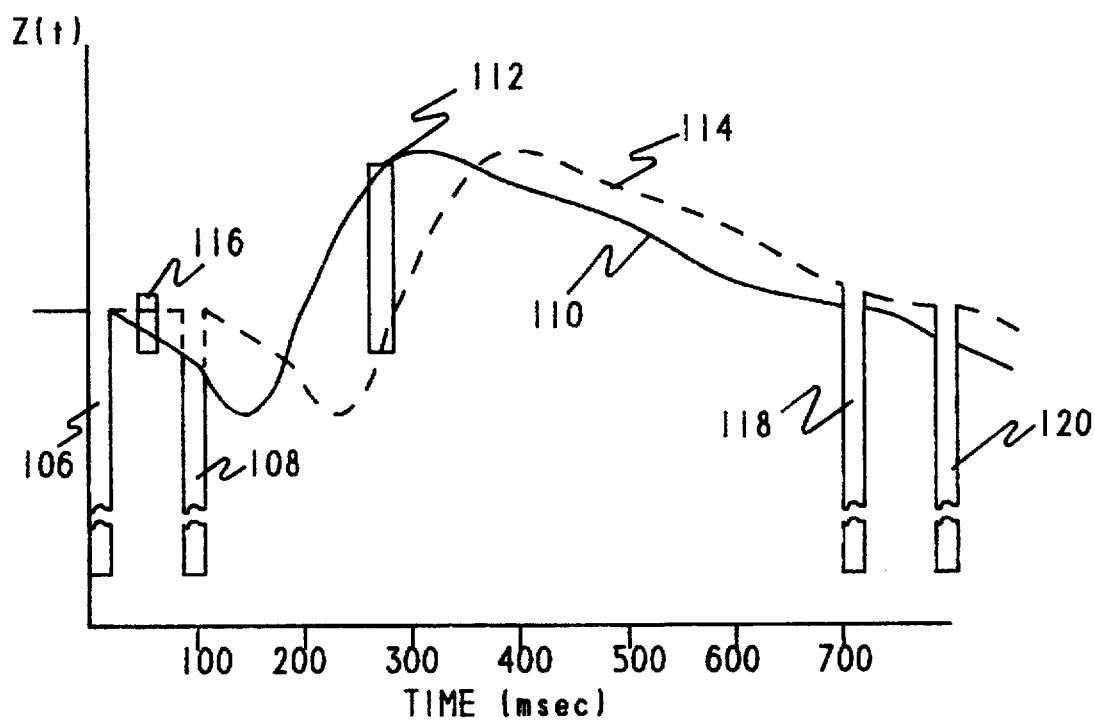
FIG. 5 is a graph of impedance using dual pulses.
Figure 6:
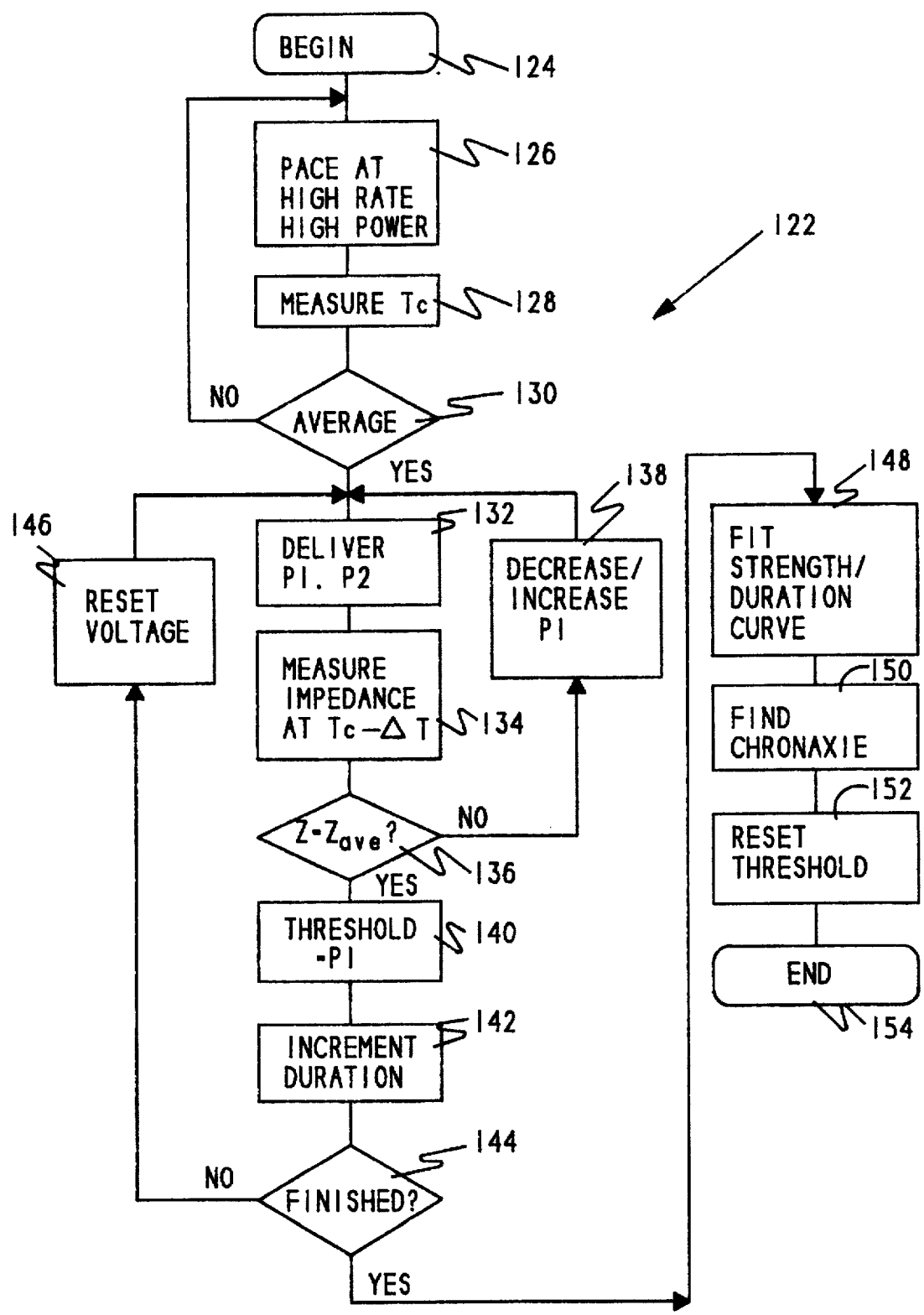
FIG. 6 is a flow chart of an algorithm for implementing our invention.

Use of recognition of a mechanical response to stimulation for autothreshold adjustment can best be understood by reference to FIGS. 4, 5 and 6. FIG. 4 illustrates a graph of the impedance response 100 of the heart over a cardiac cycle, in response to a pacing pulse 102. The pacing pulse 102 is assumed to be of a magnitude such that the heart is captured. This results in a varying impedance, associated with the mechanical pumping action of the heart which varies over about a 10 ohm range around an average impedance of about 500 ohms. After the pacing pulse 102, the impedance increases as the heart contracts and then declines again as the heart fills with blood. This contraction process lasts for about 300 msec after the delivery of the pulse 102. After a delay associated with the rate of pacing, a second pace 104 would restimulate the heart, causing another contraction. It is initially desired to determine on a case by case basis the approximate length of a time $T_C$ between a pacing pulse and a selected feature of the evoked mechanical response signal, for example, maximum impedance. This would be accomplished by applying a pacing pulse in several cycles and measuring both the impedance and elapsed time. When the impedance experienced an inflection point, that is, a local maximum, the time $T_C$ would be determined. This process would preferably be conducted over several cycles and the average of the measured $T_C$ would be utilized as a delay factor in the next part of the procedure.

Having determined a best estimate for $T_C$, the pacemaker would then determine the threshold, as illustrated in FIG. 5. A pair of pulses P1 and P2, such as pulses 106 and 108 would be delivered to the heart in each cardiac cycle by the pacemaker 10. The leading pulse 106 would be variable in either duration or strength (voltage) or both. The second or trailing pulse 108 would be of such strength and duration as to assure capture. In the course of implementing our invention, the leading pulse 106 could be either incremented or decremented as to either strength or duration, or both. Assuming that the leading pulse 106 is decremented, the pulse would initially be applied with a strength and duration great enough to assure capture of the heart. In such a situation, impedance of the heart would be detected approximately as shown by line 110. A measurement window 112 is established after the delivery of the leading pulse 106 after delay either equaled to or proportional to the predetermined time $T_C$ minus the programmed time difference between the leading pacing pulse 106 and the trailing pulse 108. Note that $T_C$ could also be selected by programmer action, utilizing the external programmer. The window 112 is of relatively short duration, on the order of 10 msec. So long as the leading pulse 106 stimulates the heart, the detected impedance difference between the impedance waveforms' baseline and that measured during period 112 would be large. As soon as the voltage of 106 declines below the threshold so that the heart is no longer stimulated to contract by the first pulse 106, the detected impedance is displaced as shown by the dotted line 114. Measurement of the impedance difference during the sampling window 112 shows a distinct drop. This phenomenon is attributable to the failure of the first pulse 106 to capture, followed by capture of the heart by the second pulse 108.

The sampling window 112 could also be of longer duration, but narrow magnitude, that is, a threshold detector active for a selected period of time. Displacement of the impedance signal from line 110 to dotted line 114 would be detected by delay in the signal crossing the threshold.

Prior art methods for determining capture by sensing impedance have tried to distinguish between a capture impedance signal or pattern and a non-capture impedance signal. Our apparatus and method by contrast, is always detecting a capture signal, but distinguishes non-capture by the temporal displacement of the capture signal from cycle to cycle.

In addition to the measurement window 112, impedance can also be measured during an initialization window 116. Subtracting the impedance measured during the initialization window 116 from the impedance measured during the sampling window 112 operates to eliminate the background or normal impedance of the body, which, as mentioned heretofore, would usually be on the order of 500 ohms. The value detected during the window 116 would be subtracted from the impedance measured during the sampling interval 112. The resulting difference would be more easily compared to recognize the shift due to failure of the first pulse 106 to capture. Thereafter, another cardiac cycle would be commenced with two more pulses 118, 120. It is desirable to determine the optimum strength and duration of a pacing pulse, as explained, for example, in U.S. Pat. No. 4,979,507. To do this, a series of tests would be performed setting the duration of the first pulse 106 to a given initial value and then varying the amplitude or voltage of the pulse 106 until loss of capture is detected, followed by incrementing or lengthening the duration of the first pulse 106 and again decrementing the magnitude of the first pulse 106 until capture were lost. A series of these tests would enable the microprocessor 14 to approximate the strength-duration curve and, as explained in U.S. Pat. No. 4,979,507, determine the optimum pacing duration and strength. It will be noted that the same result could be achieved by incrementing the first pulse 106 until capture were achieved and could also be achieved by decrementing the duration of the first pulse 106.

FIG. 6 illustrates a software program 122 which could be implemented on microprocessor 14 to detect capture according to our invention. The software program 122 would be executed by the microprocessor 14 either in response to detected changes (see Schroeppel U.S. Pat. No. 5,413,592) or on a regular basis, for example, once a day, or in response to a command from an external programmer. Software program would begin at 124 and would proceed to pace the heart 126 at a selected high power to assure capture, and at a rate, such as a relatively high rate, that would assure that the action of the heart did not itself interfere with the test, but not too high as to cause a significant drop in the amplitude of the impedance signal due to a drop in the stroke volume of the heart. By observing the rising impedance, as mentioned above, $T_c$ would be measured 128. $T_c$ represents the period of time from the pacing pulse to a distinguishing characteristic of the impedance waveform, preferably but not necessarily, the detected maximum impedance. Preferably this process would be repeated over several cycles until a suitable average 130 had been obtained. After initialization, measurement of the pacing threshold would commence with the delivery 132 of two paired pulses P1 and P2 corresponding to the first pulse 106 and the second pulse 108 of FIG. 5. Additional impedance could be measured during a first window 116 either after or between the two pacing pulses P1 and P2. After a delay of $T_c$ minus the time difference between the two pacing pulses P1 and P2 following either the first or second pacing pulses 106, 108 (in the illustrated example, following the first pacing pulse 106), the impedance of the heart would be measured 134. This impedance might then be used without further manipulation or the initial impedance during first window 116 could be subtracted in order to eliminate or reduce other effects. The microprocessor 14 would then determine 136 if the detected impedance or difference in impedance was substantially equal to the average impedance or average difference in impedance determined as explained above. If they are equal, within a preselected error, it would be assumed that capture had not been lost by the first pulse 106 and the voltage of that pulse 106 would be decremented 138. It will be apparent, of course, that the first pulse 106 could also be made very much smaller than the expected threshold and incremented until capture was achieved by the first pulse without departing from the teachings of our invention. In that case, of course, the voltage of P1 would be increased.

When the measured impedance suddenly and markedly changes from the measured average impedance, the microprocessor 14 stores 140 a threshold value equal to the magnitude of the pacing pulse P1. This value could be used for a rough approximation of the threshold, but it would also be possible to more accurately determine the optimal pacing strength and duration by utilizing the chronaxie. Assuming it was desirable to use the chronaxie, the duration of the first pulse 106 would be extended 142 (or decremented depending on the preference of the programmer) in a step wise fashion throughout a preselected range of durations. For each duration an associated threshold voltage would be determined by the microprocessor inquiring 144 whether the range of durations had been investigated and, if not, resetting the voltage 146 of the first pulse 106 and preceding to deliver another series of pulses of P1, P2 until a threshold associated with that duration had been determined. After the entire range had been sampled, microprocessor 14 would fit a strength duration curve 148 and then calculate 150 the chronaxie as explained in U.S. Pat. No. 4,979,507. From this determination, an optimum and effective strength and duration will have been selected for the operation of the pacemaker and that value of both duration and strength would be used to reset the threshold 152 plus a desired safety margin. This portion of the microprocessor programming would then end 154.

Our invention is useful in implantable cardiac stimulators, including pacemakers, for automatically determining the threshold values for stimulating the heart. Sensing a mechanical reaction of the heart, particularly through detection of the changing impedance of the heart, eliminates the need to attempt to identify a responsive electrical signal of either the R-wave or the T-wave, as has been the case in the prior art. Moreover autothreshold adjustment by impedance sensing can be utilized in both the ventricle and the atrium of the heart.

Our invention may be embodied in other specific forms without departing from the spirit or essential characteristics thereof. The foregoing description is, therefore, to be viewed in all respects as illustrative and not restrictive. The scope of our invention is defined by the appended claims.

We claim as our invention:

1. A cardiac stimulator, comprising:

at least one stimulus generator, a control circuit coupled to said generator for causing said generator to generate a sequence of paired stimuli at a selected pacing rate, a leading stimulus of each pair of the paired stimuli having an adjustable energy content beginning with an energy content on one side of the capture threshold, and a trailing stimulus of each pair of the paired stimuli always having an energy content above the capture threshold;

a circuit for adjusting the energy content of the leading stimulus toward the capture threshold;

a sensor for detecting a mechanical property of the heart during a time window at a selected time after application of at least one of said stimuli; and a circuit coupled to said sensor detecting a substantial change in magnitude in the mechanical property thereby identifying the capture threshold from the energy content of the leading stimulus.

2. The cardiac stimulator according to claim 1, wherein the sensor is an impedance sensor.

3. The cardiac stimulator according to claim 1 further comprising a circuit coupled to said controlling circuit adjusting a duration of said leading stimulus to an adjusted duration;

memory circuits coupled to said control circuitry for storing values of said leading stimulus whenever a substantial change in said mechanical property is sensed, and a microprocessor coupled to said memory circuits for calculating a chronaxie from said capture thresholds and setting a stimulus level as a function of said chronaxie.

4. The cardiac stimulator according to claim 1 wherein said sensor detects said mechanical property of the heart at a calibration time after application of at least one of said stimuli, said calibration time being shorter than said selected time, and further comprising means for eliminating a value of said mechanical property detected at said calibration time from a value of said mechanical property detected at said selected time thereby reducing measurement error.

5. A method for automatically assessing a capture threshold of an implantable pacemaker electrically coupled to cardiac tissue, comprising:

(a) generating a sequence of paired stimuli at a prescribed pacing rate, a leading stimulus of each pair of the paired stimuli having an adjustable energy content beginning with an energy content on one side of the capture threshold, and a trailing stimulus of each pair of the paired stimuli always having an energy content above the capture threshold;

(b) applying the sequence of paired stimuli to the cardiac tissues while adjusting the energy content of the leading stimulus toward the capture threshold;

(c) detecting a mechanical property of the heart during a time window at a selected time after application of at least one of said stimuli; and (d) defining the capture threshold to be approximately equal to the energy content of the leading stimulus of the leading stimulus of the paired stimuli that immediately precedes a substantial change in magnitude in the detected mechanical property.

6. The method according to claim 5, wherein the detected mechanical property is the impedance of the heart.

7. The method according to claim 6 wherein the energy content of the leading stimulus is decreased.

8. The method according to claim 7 wherein the voltage of the leading stimulus is decreased.

9. The method according to claim 5 wherein the energy content of the leading stimulus is decreased.

10. The method according to claim 9 wherein the voltage of the leading stimulus is decreased.

11. The method according to claim 5 further comprising (e) adjusting a duration of said leading stimulus to an adjusted duration;

(f) detecting at least one additional capture threshold associated with said adjusted duration;

(g) calculating a chronaxie from said capture thresholds; and (h) setting a stimulus level as a function of said chronaxie.

12. The method according to claim 5 further comprising detecting said mechanical property of the heart at a calibration time after application of at least one of said stimuli, said calibration time being shorter than said selected time, and eliminating a value of said mechanical property detected at said calibration time from a value of said mechanical property detected at said selected time thereby reducing measurement error.

13. The method according to claim 5 further comprising measuring a period of time from a stimulus to a selected feature of said mechanical property and setting said selected time as a function of said period of time.

14. The method according to claim 13 wherein the step of measuring a period of time comprises measuring a plurality of periods over a plurality of cardiac cycles and combining said plurality of periods to determine said period of time.

15. An implantable cardiac pacemaker comprising:

(a) means for generating a sequence of paired stimuli at a prescribed pacing rate, a leading stimulus of each pair of the paired stimuli having an adjustable energy content beginning with an energy content on one side of the capture threshold, and a trailing stimulus of each pair of the paired stimuli always having an energy content above the capture threshold;

(b) means for applying the sequence of paired stimuli to the cardiac tissues and for adjusting the energy content of the leading stimulus toward the capture threshold;

(c) means for detecting a mechanical property of the heart during a time window at a selected time after application of at least one of said stimuli; and (d) means for defining the capture threshold to be approximately equal to the energy content of the leading stimulus of the leading stimulus of the paired stimuli that immediately precedes a substantial change in magnitude in the detected mechanical property.

16. The cardiac pacemaker according to claim 15, wherein the means for detecting a mechanical property is means for detecting the impedance of the heart.

17. The cardiac pacemaker according to claim 16 wherein the means for adjusting the energy content of the leading stimulus is means for decreasing the energy content of said leading stimulus.

18. The cardiac pacemaker according to claim 17 wherein the means for decreasing the energy content is means for decreasing the voltage of the first stimulus.

19. The cardiac pacemaker according to claim 15 wherein the means for adjusting the energy content of the leading stimulus is means for decreasing the energy content of the leading stimulus.

20. The cardiac pacemaker according to claim 19 wherein means for decreasing the energy content is means for decreasing the voltage of the leading stimulus.

21. The cardiac pacemaker according to claim 15 further comprising
   (e) means for adjusting a duration of said leading stimulus to an adjusted duration;
   (f) means for detecting at least one additional capture threshold associated with said adjusted duration;
   (g) means for calculating a chronaxie from said capture thresholds; and
   (h) means for setting a stimulus level as a function of said chronaxie.

22. The cardiac pacemaker according to claim 15 further comprising means for detecting said mechanical property of the heart at a calibration time after application of at least one of said stimuli, said calibration time being shorter than said selected time, and means for eliminating a value of said mechanical property detected at said calibration time from a value of said mechanical property detected at said selected time thereby reducing measurement error.

* * * * *